United States Patent [19]

Tiger

[11] 4,412,537

[45] Nov. 1, 1983

[54] FRESH AIR BREATHING MASK WITH EXTERIOR HEAT EXCHANGER

[76] Inventor: Howard L. Tiger, Eagle Ridge Way, West Orange, N.J. 07052

[21] Appl. No.: 287,309

[22] Filed: Jul. 27, 1981

[51] Int. Cl.³ .............................................. A61M 15/00
[52] U.S. Cl. ............................ 128/204.17; 128/207.13
[58] Field of Search ...................... 128/201.13, 204.15, 128/204.17, 207.13, 139

[56] References Cited

U.S. PATENT DOCUMENTS

| | | | |
|---|---|---|---|
| 603,021 | 4/1898 | Dight | 128/201.13 |
| 812,706 | 2/1906 | Warbasse | 128/207.13 |
| 1,281,211 | 10/1918 | Rogers | 128/139 |
| 2,468,383 | 4/1949 | Tiffany | 128/201.13 |
| 4,269,183 | 5/1981 | Hunt | 128/204.17 |

Primary Examiner—Henry J. Recla
Attorney, Agent, or Firm—Charles E. Baxley

[57] ABSTRACT

A typical embodiment of the invention provides a sturdy, lightweight, inexpensive and comfortable warmer for fresh breathing air. An heat exchanger that is sufficiently flexible to conform with the shape of a wearer's scalp is secured to the wearer's head by means of a pullover cap. In this way the heat exchanger takes advantage of the great heat dissipating capabilities of the human head in order to warm fresh breathing air on its way from the atmosphere to the wearer's nose mask.

1 Claim, 1 Drawing Figure

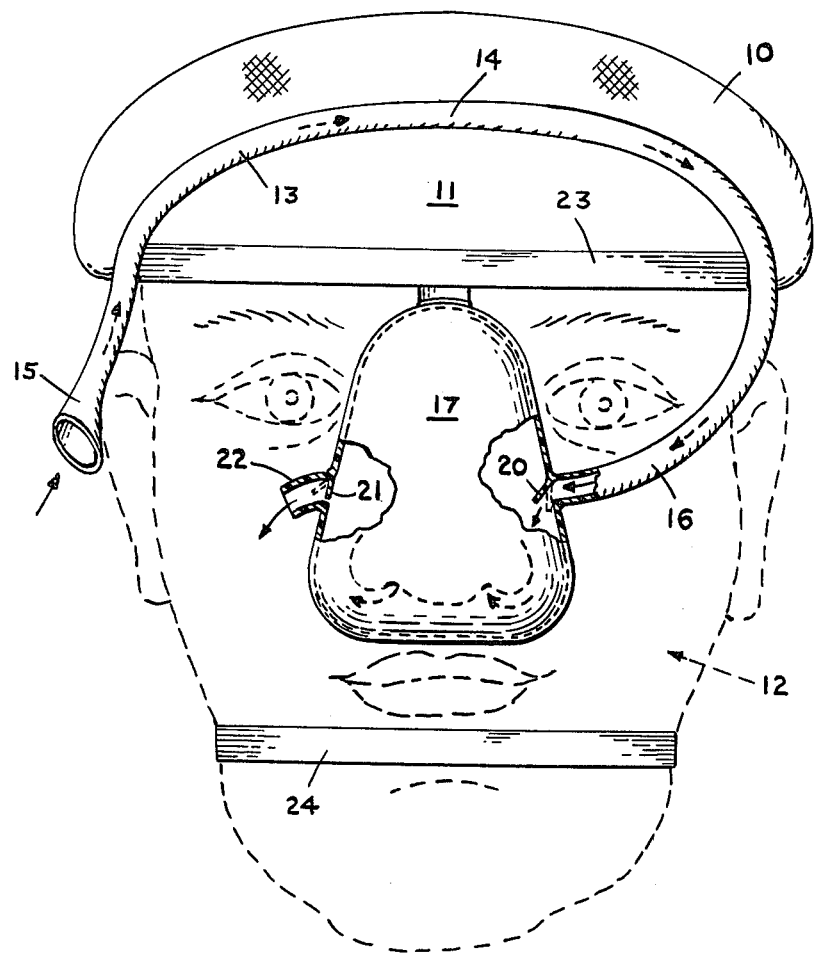

FRESH AIR BREATHING MASK WITH EXTERIOR HEAT EXCHANGER

This invention relates to apparatus for preheating air prior to inspiration and, more specifically, to an apparatus for applying body heat to fresh cold air in order to warm the air prior to inhalation.

BACKGROUND OF THE INVENTION

There is a need in the art for comfortable, convenient and inexpensive means for prewarming air for breathing. For example, in the case of persons suffering from cardiac insufficiency, whether congenital or acquired as a result of heart damage resulting from injury or disease, the patient is commonly advised to engage in moderate exercise, as tolerated. One of the best of such exercises is walking, which is of course normally an outdoor activity. This, however, may lead to problems, particularly in cold weather. Under cold conditions, the heart is doubly stressed—partially by the physical demand on the muscles, requiring increased circulation to carry away lactic acid and other waste products or muscular activity, and partially by the additional increased circulation required to maintain the body temperature at a proper level. The latter stress does not signal its presence by muscular discomfort, as does the former, and the result is that the patient is unconsciously placing greater demands on his heart than he should. The same effect is commonly experienced by persons having no previous history of cardiac problems, as one is reminded every year by an upswing in incidence of heart attacks which can be directly associated with heavy exercise such as snow shovelling during periods of cold weather. One of the most direct mechanisms whereby the body is chilled is by inhalation of cold air which not only chills the tissues forming the walls of the components of the respiratory tract, but also chills the bloodstream itself by heat transfer which takes place in the alveole concurrently with the oxygenation of oxygen-depleted blood from the pulmonary artery. Thus, the demands placed on the heart for maintenance of body temperature can be alleviated and the above mentioned problems can be overcome to an appreciable degree, by preheating air before it is inspired into the body.

Previous attempts to solve this problem have generally taken the form of interposing a porous barrier, for example of knit wool or spongy polymer, between the nose and/or mouth of the user and the external atmosphere. While successful to a degree, such measures suffer from certain disadvantages. For example, the interposed porous material necessarily involves some resistance to free air flow, and to that extent makes breathing more difficult. Also, there is an annoying tendency for moisture in exhaled breath to condense on contact with the cold ambient atmosphere, and to deposit as moisture or as ice crystals on the surface and in the pores of the porous material, creating a most uncomfortable condition. Perhaps, more importantly, the mechanism whereby the warming of incoming air is accomplished is by direct heat exchange with warm exhaled air in the porous material. This necessitates that a certain amount of the exhaled air be trapped in the porous material, mixed with fresh incoming air to accomplish the desired heat exchange, and then reinhaled as part of the mixture. This, in turn, defeats pro tanto the advantage of the heat exchange, inasmuch as the mixture being breathed has already been partially depleted of oxygen, so that additional quantities of the mixed gases must be inhaled in order to maintain the required oxygen supply.

The following patents are illustrative of prior art efforts to solve these problems.

U.S. Pat. No. 909,979 granted Jan. 19, 1909 to E. E. Zerkle for "Respiratory Apparatus" fails to disclose any means for warming the fresh intake air.

U.S. Pat. No. 2,344,920 granted Mar. 21, 1944 to G. P. Maggi for "Frost Mask" shows heat exchanging tubes that pass through a warm chamber inside a mask in which the incoming air is subjected only to a small temperature gradient within one or more tubes of limited heat transfer surface.

U.S. Pat. No. 3,249,108 granted May 3, 1966 to L. A. Terman for "Mask for Protecting Respiratory Tract" shows an electrical or chemical heating element within a face mask to warm fresh, cold air that is drawn into the apparatus.

U.S. Pat. No. 3,491,754 granted Jan. 27, 1970 to W. W. Weese for "Methods and Apparatus for Facilitating Respiration" shows a multiple layered heat exchanger for warming fresh air prior to inhalation by the wearer through a mouth piece.

U.S. Pat. No. 3,707,966 granted Jan. 2, 1973 to J. A. Nebel for "Personal Breathing Apparatus" shows a chest pad for preheating breathing air that is supplied to a face mask through a flexible conduit.

U.S. Pat. No. 4,062,359 granted Dec. 13, 1977 to M. E. Geaghan for "Low Temperature Breathing Apparatus" relies on a porous tube that can be placed between the body and adjacent clothing to preheat air that is being inhaled.

U.S. Pat. No. 4,150,671 granted Apr. 24, 1979 to H. T. Tiger for "Warm Air Weathermask" uses exhaled breath as a source of warmth for the incoming cold air.

Further in this respect a clinical study by E. N. Schachter, M.D., Elliot Tack and Marjorie Lee, M.D. published by Home Health Care Products, Medical Products Division/3M, 555-1S, 3 M Center, St. Paul, Minn. 55101 in April 1979 and titled "3M Cold Weather Research Data & Results" describes a number of tests conducted on young asthmatics using, presumably, the 3M cold weather mask which is formed from soft foam material that is supposed to warm and moisten inhaled air.

All of these foregoing designs have a number of flaws or disadvantages, some of which have been considered at some length above. The porous nose mask, for example, produces a great deal of moisture condensation and rebreathing of exhaled air. Those devices, moreover, which couple the mouth or nose piece to a heat exchanger through flexible tubing are unsatisfactory for other reasons. Hand mobility is seriously impeded with these tube devices. The additional weight of the tube, stretched as it is between the heat exchanger and the mouth or nose piece places a further and uncomfortable strain on the neck muscles. The exposed span of tubing between the wearer's body and the mouth or nose piece provides a major locus for lost heat. The chest and back of the wearer also are not necessarily the best radiators of body heat, nor is the location of the heat exchanger, buried under layers of clothing, a suitable location for the air inlet to an heat exchanger because of the pressure loss and attendant fatigue in respiration that is experienced when inhaling air through this resistance.

Accordingly, there is a need for a device that warms cold air through body heat without introducing inordinate breathing resistance, heat loss or discomfort.

SUMMARY OF THE INVENTION

These and a number of other problems that have beset the prior art are overcome, to a large extent, through the practice of the invention. Illustratively, a flexible heat exchanger is secured under a cap in order to be pressed against the wearer's head. The heat exchanger establishes fluid communication between the atmosphere and a nose piece by way of a one way check valve that opens during the inhalation phase of the breathing cycle. Exhaled air is discharged from the nose piece directly into the atmosphere, also by way of a check valve that opens during the exhalation phase of the cycle.

In this manner, the invention takes advantage of the fact that the head is a primary source of body heat dissipation, thereby providing over the surface of the scalp not only an improved temperature gradient for warming the incoming air, but a large heat transfer area for promoting this warming action. The relatively short length of tube between the heat exchanger and the nose piece reduces the heat loss to the atmosphere from the tube, reduces the weight of the apparatus, improves the mobility of the wearer's head, relieves the strain on the wearer's neck muscles and reduces the pressure loss that otherwise must be overcome in the breathing cycle.

These and other features of the invention will be apparent in greater detail through a study of the following description of a specific embodiment of the invention. The scope of this invention, however, is limited only through the claims appended hereto.

BRIEF DESCRIPTION OF THE DRAWING

The sole FIGURE of the drawing is a front elevation in full section of a typical embodiment of the invention as worn in use.

DETAILED DESCRIPTION

As illustrated in the drawing a woolen pullover cap 10, or the like, fits snugly over scalp 11 of a wearer 12. Interposed, however, between the cap 10 and the scalp 11 is a flat, flexible heat exchanger 13.

As shown in the drawing, the heat exchanger 13 generally conforms to the shape of the crown of the wearer 12. Accordingly, the heat exchanger 13 covers a good part of the scalp 11 in order to offer a maximum heat transfer area. The heat exchanger 13 further is thin to fit comfortably on the scalp 11 and to remain in place while jogging or the like without imposing a need for a too tight fit between the cap 10 and the heat of the head of the wearer 12.

In these circumstances, heat exchanger 13 can be formed of a suitably flexible and heat-conducting plastic or rubber.

Within the heat exchanger 13 air passageways 14 are formed to enable air within the heat exchanger to absorb heat from the scalp 11, thereby improving the thermal absorption features of the invention and providing a superior thermal gradient for warming the air in the heat exchanger.

The air passageways 14 are in fluid communication with the atmosphere by means of fresh air inlet 15 that protrudes from beneath the cap 10 in order to draw freely from the ambient air. The heat exchanger 13 also establishes fluid communication for warmed air within the passageways 14 through a short length of flexible tube 16 to a nose mask 17 by way of a check valve 20. The check valve 20 opens to establish fluid communication with the atmosphere by way of the tube 16, the heat exchanger 13 and the fresh air inlet 15 during those times in which low pressure is created within the mask 17 during the inhalation phase of the normal breathing cycle. Clearly, in these circumstances, the nose mask 17 must fit snugly, albeit comfortably against the face of the wearer 12 in order to eliminate, in general, air flow into the nose mask through leakage between the face of the wearer 12 and the adjacent periphery of the mask. In this manner, essentially all of the air that is drawn into the nose mask 17 has been warmed by means of passage through the flexible heat exchanger 13.

In the exhalation phase of the normal breathing cycle, higher pressure within the nose mask 17 closes the check valve 20 and prevents exhaled air from entering the tube 16 and the heat exchanger 13. This higher pressure, however, does open hertofore closed check valve 21. The exhaled air then flows through the now opened valve 21 and through a short discharge tube 22 to the atmosphere.

The nose mask 17, as shown in the drawing is secured to the wearer 12 by means of adjustable straps 23, 24 that are fastened snugly, but comfortably about the head of the wearer. Naturally, a complete or partial face mask can be substituted for the nose mask 17, if required.

In operation, the wearer 12 secures the nose mask 17 to his face by positioning and tightening the straps 23, 24 in the positions shown in the drawing. The cap 10 and heat exchanger 13 that is secured within the cap are pulled snugly down over the scalp 11 to permit the flexible heat exchanger to conform to the shape of the wearer's scalp 11 and to establish a good thermal contact with the scalp. The wearer 12 inhales normally, therby creating a low pressure within the nose mask 17 that closes the discharge check valve 21 and opens the inlet check valve 20.

The combination of low pressure in the nose mask 17 and open check valve 20 causes higher pressure air in the atmosphere to flow into the nose mask through the fresh air inlet 15, the heat exchanger 13 and the tube 16. While flowing through the heat exchanger passageways 14, the fresh air is heated by means of thermal conduction from the scalp 11 and thus is suitably warmed when it flows into the nose mask 17.

Upon exhaling, the check valve 20 is closed by the high pressure within the nose mask 17, thereby barring all but a very small amount of exhaled air from entering the tube 16. This high pressure of exhaled air within the nose mask 17 does compel the check valve 21 to open, thus enabling the exhaled air to flow through the opened valve 21, and the discharge tube 22 into the atmosphere.

Accordingly, the invention provides a relatively inexpensive, sturdy, lightweight and comfortable apparatus for efficiency utilizing body heat to warm breathing air. There are, of course, many modifications that are possible and within the scope of the invention. The cap 10, for instance, can be an integral part of the heat exchanger 13, or entirely eliminated. In this latter case, however, heat losses through the exposed surface of the heat exchanger 13 may be prohibitive in the absence of suitable insulation.

I claim:

1. A breathing mask for wear on the head comprising a tubular fresh air inlet, a heat exchanger in fluid communication with said fresh air inlet, said heat exchanger being sufficiently flexible to conform with the scalp and being generally thin in order to absorb heat from the scalp, a flexible tube in fluid communication with said heat exchanger, and a check valve for selectively interrupting said flexible tube fluid communication to establish air flow only from said heat exchanger through said flexible tube, a nose mask in fluid communication with said tube and said check valve, another check valve for establishing fluid communication with said mask, a discharge tube for providing fluid communication selectively from said mask and directly to the atmosphere through said another check valve, a cap for securing said heat exchanger to the head, and means for securing said mask to the head.

* * * * *